United States Patent [19]

Zhao

[11] Patent Number: 5,420,366
[45] Date of Patent: May 30, 1995

[54] PROCESS FOR THE PREPARATION OF OPTICALLY ACTIVE 2-ARYLCYCLOHEXANOLS

[75] Inventor: Shu-Hai Zhao, Corpus Christi, Tex.

[73] Assignee: Hoechst Celanese Corporation, Somerville, N.J.

[21] Appl. No.: 241,322

[22] Filed: May 11, 1994

[51] Int. Cl.$^6$ .................. C07C 35/08; C07C 35/00
[52] U.S. Cl. .................. 568/832; 568/814; 568/817; 568/819; 568/822; 568/834
[58] Field of Search ............... 568/814, 817, 819, 822, 568/832, 834

[56] References Cited

U.S. PATENT DOCUMENTS

| | | | |
|---|---|---|---|
| 4,871,855 | 10/1989 | Marko et al. | 546/134 |
| 4,965,364 | 10/1990 | Marku et al. | 546/134 |
| 5,002,776 | 3/1991 | Geoghegan et al. | 424/497 |
| 5,008,411 | 4/1991 | Coffeu et al. | 549/519 |
| 5,126,494 | 6/1992 | Giheany et al. | 568/807 |

FOREIGN PATENT DOCUMENTS 5-246918  9/1993  Japan.

OTHER PUBLICATIONS

Tetrahedron Asymmetry, 1992, 3 1029. Tetrahedron Letters, Aug. 1, 1994, vol. 35, No. 31, pp. 5611–5612.

*Primary Examiner*—Werren B. Lone
*Attorney, Agent, or Firm*—James J. Mullen; Donald R. Cassady

[57] ABSTRACT

The present invention provides a process for preparing optically active 2-arylcyclohexanol and its esters and ethers and which process comprises the step of subjecting 1-aryl-cyclohexane-1,2 diol and its diethers and diesters to hydrogenolysis conditions to form said cyclohexanol and its esters and ethers.

20 Claims, No Drawings

PROCESS FOR THE PREPARATION OF OPTICALLY ACTIVE 2-ARYLCYCLOHEXANOLS

BACKGROUND OF THE INVENTION

1. Field of the Invention

The present invention relates to processes for preparing optically active 2-aryl cyclohexanols which are important as chiral sources for asymmetric transformations or as chiral materials for asymmetric manufacturing of physiologically active substances such as diltiazem.

2. Description of Related Art

The following prior art references are disclosed in accordance with the terms of CFR 1.56, 1.97, and 1.98.

U.S. Pat. No. 4,871,855 (Oct. 3, 1989) discloses an asymmetric dihydroxylation of a wide variety of olefins.

U.S. Pat. No. 4,965,364 (Oct. 23, 1990) discloses an asymmetric dihydroxylation of a wide variety of olefins.

U.S. Pat. No. 5,002,776 (Mar. 26, 1991) discloses controlled absorption pharmaceutical formulations containing diltiazem.

U.S. Pat. No. 5,008,411 (Apr. 16, 1991) discloses a process of preparing (−)-(1R,2S)-2-phenylcyclohexanol from (+)-trans-2-phenylcyclohexanol chloroacetate using a lipase from pseudonomas fluoresens.

U.S. Pat. No. 5,126,494 (Jun. 30, 1992) discloses methods for catalytic asymmetric dihydroxylation of olefins.

Japanese patent application 5246918 (Sep. 24, 1993) discloses optically active trans-2-arylcyclohexanol derivatives prepared by ester exchange between 2-aryl-1-cyclohexanol and fatty acid, vinyl esters, or triglycerides in the presence of esterase.

Organic Synthesis, 1990, volume 69, page 1 discloses a process for preparing phenyl cyclohexanol from cyclohexene oxide and phenylmagnesium bromide using a step which employs Lipase.

Tetrahedron Asymmetry, 1992, 3, 1029 discloses asymmetric hydrosilylation of 2-phenylcyclohexanone.

All of the above-cited prior art patents and articles are incorporated herein by reference in their entirety.

SUMMARY OF THE INVENTION

The present invention provides a process for preparing optically active 2-arylcyclohexanol and its esters and ethers and which process comprises the step of subjecting optically active 1-aryl-cyclohexane-1,2-diol and its diethers and diesters to hydrogenolysis conditions to form said cyclohexanol and its esters and ethers.

DETAILED DESCRIPTION OF THE INVENTION

In conjunction with the prior art set forth above, it can readily be seen that, in the past, there was no simplified method, outside of resolution chemistry, to prepare optically active 2-arylcyclohexanols. In accordance with the present invention, optically active aryl cyclohexane-1,2-diols, ("diols") and diethers and diesters thereof can be directly convened to optically active 2-arylcyclohexanols ("alcohols") and the ethers and esters thereof by subjecting the diols to hydrogenolysis. Furthermore, not only can one produce the "trans" form, but the "cis" form can also be prepared by the present invention process.

The starting materials used in the present invention process are the optically active 1-aryl-cyclohexane-1,2-diols and diethers and diesters thereof as illustrated by the formula:

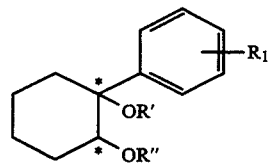

(I)

wherein $R_1$ is hydrogen; a $C_1$ to $C_{15}$ alkyl group; allyl group; cyclohexyl group; benzyl group; 9-anthrylmethyl group; t-butyldimethylsilyl group; phenyl group; naphthyl group; halogens such as chlorine, bromine, fluorine; $NO_2$; $NR_2R_3$ where $R_2$ and $R_3$ are each independently H or $C_1$ to $C_{15}$; $SO_3R_4$ where $R_4$ is H or $C_1$ to $C_{15}$; $-N(R_5)-C(O)-R_6$ where $R_5$ and $R_6$ are each independently H or $C_1$ to $C_{15}$; $-O-C(O)-R_7$ where $R_7$ is H or $C_1$ to $C_{15}$; $OR_8$ where $R_8$ is H or $C_1$ to $C_{15}$ such as methoxymethyl group; methoxyethyl group; methylthiomethyl group; tetrahydropyranyl group; cyclopropylmethyl group; and $R'$ and $R''$ are each independently selected from the group H, $C_1$ to $C_{15}$; $-C(O)-R'''$ where $R'''$ is H, $C_1$ to $C_{15}$ or halogenated $C_1$ to $C_{15}$ (e.g. $-C(O)-CH_2Cl$).

$R_1$, taken together with the benzene ring to which it's attached, can also be naphthalene, anthracene, phenanthrene, and pyridine. All of the compounds falling within Formula I will be referred to as "diols" herein.

The desired end products formed by the novel processes of the present invention are the optically active 2-aryl-1-cyclohexanols and esters and ethers thereof as illustrated by the formula:

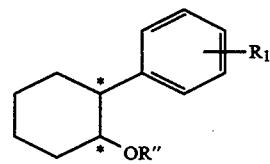

(II)

wherein $R_1$ and $R''$ are the same as $R_1$ and $R''$ in Formula I above.

All of the compounds falling within the Formula II may sometimes be referred to as "alcohols" herein, notwithstanding the fact that esters and ethers are covered.

In conjunction with the structural formulae of I and II above, asterisk (*) means the carbon centers are chiral.

In the hydrogenolysis step, hydrogen can be supplied, in the form of hydrogen gas.

In conjunction with the hydrogenolysis step, a catalyst is employed to facilitate the reaction. Catalysts for this function include those of the transition metal type, or a reduced salt of such metal on a suitable support. Any metal from Group VIII, Periodic Table of Elements, can be used. Examples of transition metals include palladium, platinum, ruthenium, rhodium, iridium, copper, nickel, cobalt, osmium, and combinations thereof.

Some suitable supports for the transition metals include, without limitation, carbon, alumina, silica, barium sulfate, and polymeric resins.

Non-exclusive examples of catalysts include Pd/C, Pt/C, Pt/Al$_2$O$_3$, copper chromite, Raney nickel, and Raney cobalt.

Where the aryl group of the above-described diol (Formula I) is halogenated, it may be desirable to use a Lincilar catalyst, e.g. palladium on barium sulfate, to insure halogen stability.

There is no restriction or limitation on the type of catalyst or material which can be used to effect the hydrogenolysis and thus produce the desired end product.

Another facet of the present invention is the unique ability to form separately the "cis" and "trans" forms of the aryl cyclohexanols (alcohols) from the same optically active diol. In addition, these alcohols are also optically active and this has not been accomplished by the prior an up to the date of the present invention. As previously mentioned, the prior art has disclosed various methods for preparing the "trans" alcohols but has not been able to prepare separately the "cis" and "trans" optically active alcohols using the same starting material, i.e. optically active diols. In this regard, the use of a particular catalyst (of the materials disclosed herein) provides a novel process route in the hydrogenolysis procedure to effect the production of the optically active alcohol and either the cis or the trans isomers. As will be seen in the examples set forth herein, the catalyst selection is important in order to prepare the desired stereo form.

The catalyst is present in the hydrogenolysis step in any amount which will facilitate achieving the desired end result. Thus, the catalyst can be employed in an amount of from about 0.001% to about 4000% (or more) by weight, based on the weight of said diol being treated. In some instances, one may use sufficient quantities of Raney nickel without the need to have any other source of hydrogen. In this situation, Raney nickel, as commercially supplied, has sufficient quantities of hydrogen to promote the hydrogenolysis of the diol to produce the alcohol.

Where one so desires to greater facilitate the reaction, it is also within the scope of the present invention to employ a co-catalyst such as a mineral acid, e.g. HCl and H$_2$SO$_4$.

In the hydrogenolysis step, one may employ a solvent in order to facilitate the reaction and the overall handling aspects thereof. A suitable or appropriate solvent is any one which does not substantially interfere with or hinder achieving the desired end result. Also, the solvent must have a melting point and boiling point placing it in the liquid state under the conditions employed for the hydrogenolysis reaction of the process. The solvent is a basic organic solvent, such as, for example, alcohols, esters, acids and the like, and mixtures thereof.

Such solvents include, without limitation, an alkyl-carboxylic acid such as formic acid, acetic acid, propanoic acid, butanoic acid, 2-methylpropanoic acid, isobutyric acid, pentanoic acid, 2-2-dimethylpropanoic acid, and heptanoic acid; lower alkyl esters such as methylacetate, ethylacetate, and propylacetate; lower alkyl alcohols such as methanol, ethanol, propanol, and n-butanol; an aqueous alcohol; toluene; diethyl ether; tetrahydrofuran; 1,4-dioxane; water; amides such as DMF and NMP; and mixtures and/or combinations of any one or more of these solvents.

The solvent is present in the hydrogenolysis step in an amount sufficient to facilitate the reaction and/or handling of the reactants.

The hydrogenolysis step is generally conducted at a temperature of from about 0° C. to about 300° C., preferably from about 15° C. to about 80° C. However, lower or higher temperatures can be employed where one so desires.

The hydrogenolysis step is generally conducted at a pressure of from about one atmosphere to about 200 atmospheres, preferably from about five to about eighty atmospheres.

The hydrogenolysis step is generally conducted for a sufficient period of time to permit the diol to form the alcohol. Such time can be from one hour to about 48 hours but generally will be from about two hours to about 24 hours.

In general, the cis and trans 2-aryl-1-cyclohexanols can be prepared by the following Scheme 1 which shows, for example, the preparation of both the cis and trans 2-phenylcyclohexanol.

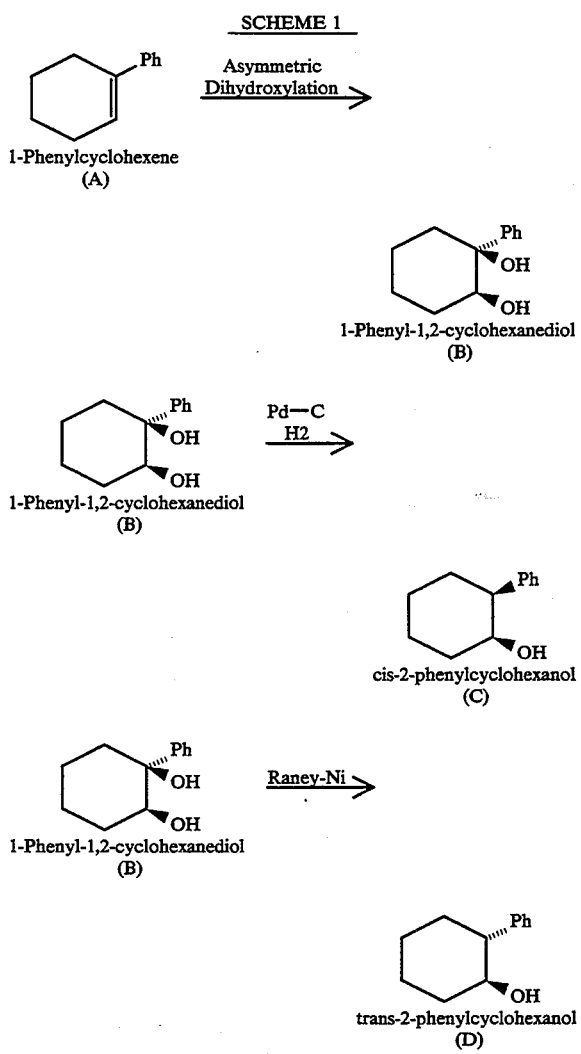

In Scheme I above, 1-phenyl-cyclohexene (A) is asymmetrically dihydroxylated with a chiral osmium catalyst to give optically active 1-phenyl-1,2-cyclohexanediol (B), enriched in either (1S,2S) or (1R,2R) enantiomer, depending on the chiral ligand employed.

The optically active 1-phenyl-1,2-cyclohexanediol (B) is then subjected to hydrogenolysis conditions using either Pd-Carbon or Raney nickel catalyst with hydrogen pressure of 0–15 atm in a solvent at 20°–150° C. to give optically active cis-2-phenylcyclohexanol (C) or trans-2-phenyl-cyclohexanol (D), respectively. The formation of different stereoisomers of 2-phenylcyclohexanol in the hydrogenolysis of 1-phenyl cyclohexane-1,2-diol depends on the stereostructure of the diol and the catalyst employed as depicted below:

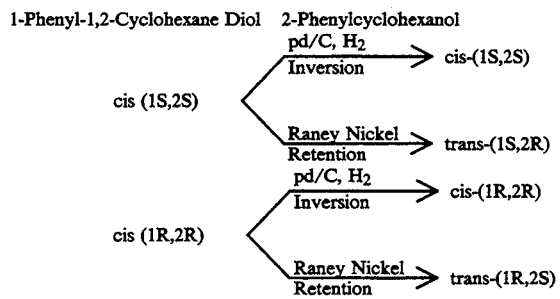

The desired products can be isolated and purified by chromatography, distillation, or recrystallization.

Compound (B) is known and can be prepared according to literature procedure as follows: (1S,2S)-1-phenyl-1,2-cyclohexanediol A 1-L flask equipped with a mechanical stirrer, was charged with 250 mL of t-BuOH, 250 mL of water, 70 g of AD-mix-α (Aldrich) and methanesulfonamide (4.75 g, 50 mmol). The mixture was cooled to 0° C. while stirring. 1-Phenyl-cyclohexene (Aldrich, 7.9 g, 7.95 ml, 50 mmol) was added at once and the mixture was stirred at 0° C. for 16 hours. $Na_2SO_3$ (75 g) was added at 0° C. and stirring continued for another two hours. After separation of layers, the aqueous phase was extracted with ethyl acetate (2×200 mL). Combined organic phase was washed with aqueous NaOH, dried over $MgSO_4$, filtered, and concentrated to give the title compound as white solids (9.9 g, ee>97%). This diol could be further purified by column chromatography on silica gel (eluant: $EtOAc/CH_2Cl_2$, ¼).

Other 1-phenyl-1,2-cyclohexanediols, i.e. substituted on the phenyl ring with $R_1$ (defined in Formula I above) can be prepared in a similar manner. The esters and ethers thereof can be prepared by subsequent esterification or alkylation of the diols.

The following specific examples are supplied for the purpose of better illustrating the invention. These examples are not intended, however, to limit or restrict the scope of the invention in any way, and should not be construed as providing conditions, parameters, or values which must be utilized exclusively in order to practice the present invention.

EXAMPLE 1

Preparation of Cis-(1S,2S)-2-phenylcyclohexanol

A reactor was charged with Pd on carbon (10%, 0.5 g), 0.5 mL of concentrated HCl and 100 mL of MeOH. (1S,2S)-1-Phenyl-1-2-cyclohexanediol (1.92 g, 10 mmol) was added and the reactor was sealed and purged with $N_2$, then kept under $H_2$ (200 psi) at 60° C. under stirring for four hours. GC and GC-MS analysis of the crude reaction mixture showed disappearance of the starting diol and formation of the desired product. Purification by column chromatography on silica gel (Hexanes-/EtOAc 7/1) gave 1.15 g of white solids (65%). NMR indicated it was the cis-2-phenylcyclohexanol by comparison with literature data. The specific rotation $[\alpha]22_D$ was +109.1 (C=0.24, MeOH).

EXAMPLE 2

Preparation of Trans-(1S,2R)-2-Phenyl-Cyclohexanol

A mixture of (1S,2S)-1-phenyl-1,2-cyclohexanediol (470 mg, 2.4 mmol) and Raney nickel (400 mg) in 50 mL of ethanol was stirred at 60° C. under hydrogen (pressure at 790 psi) for 24 hours. GC analysis of the crude reaction mixture indicated the formation of trans-(1S,2R)-2-phenylcyclohexanol (15%) and the unreacted starting material (85%).

EXAMPLE 3

Preparation of Trans-(1S,2R)-2-Phenyl-Cyclohexanol

This example demonstrates the use of Raney nickel as both the catalyst and as a supplier of $H_2$ for the hydrogenolysis.

A mixture of (1S,2S)-1-phenyl-1-2-cyclohexanediol (384 mg, 2 mmol) and Raney nickel (15 g) in 80 mL of ethanol was stirred at room temperature at 50° C. for 24 hours. The progress of the reaction was followed by GC and TLC (EtOAc/Hexanes 1/5). The mixture was filtered and concentrated. The crude product was purified by column chromatography. The title compound was obtained as white solids (210 mg, 60%). Specific rotation $[\alpha]_D$=52.6 (c=0.81 in MeOH). LC, using a chiral column, showed that the (1R,2S) enantiomer was below the detectable limit (ee>95%)

EXAMPLES 4–13

Using the procedure set forth in Example 3 above, the following compounds (falling within Formula II) are prepared as follows:

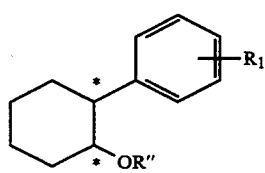

(II)

| Example No. | R″ | $R_1$ | Compound No./Name |
|---|---|---|---|
| 4 | H | OH | (1S,2R)-trans-2-(2-hydroxyphenyl)-1-cyclohexanol |
| 5 | H | —OCH₃ | (1S,2R)-trans-2-(3-methoxyphenyl)-1-cyclohexanol |
| 6 | H | —OC₃H₆ | (1S,2R)-trans-2-(2-propyloxyphenyl)-1-cyclohexanol |
| 7 | H | —OC₄H₈ | (1S,2R)-trans-2-(4-tert-butoxyphenyl)-1-cyclohexanol |

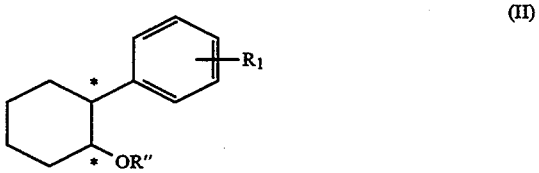

| Example No. | R" | $R_1$ | Compound No./Name |
|---|---|---|---|
| 8 | H | —Cl | (1S,2R)-trans-2-(3-chlorophenyl)-1-cyclohexanol |
| 9 | H | —$NH_2$ | (1S,2R)-trans-2-(3-aminophenyl)-1-cyclohexanol |
| 10 | H | —O—C(O)—$CH_3$ | (1S,2R)-trans-2-(3-acetoxyphenyl)-1-cyclohexanol |
| 11 | —$CH_3$ | H | (1S,2R)-trans-2-(phenyl)-1-cyclohexyl methyl ether |
| 12 | —C(O)$CH_3$ | H | (1S,2R)-trans-2-(phenyl)-1-cyclohexyl acetate |
| 13 | —C(O)$CH_2$Cl | H | (1S,2R)-trans-2-(phenyl)-1-cyclohexyl chloroacetate |

Finally, the optically active products of the process of this invention have a wide range of utility that is well known and documented in the prior art, e.g. they are especially useful as chiral sources for asymmetric induction, pharmaceuticals, flavors, fragrances, agricultural chemicals, and the like. Illustrative therapeutic applications include, for example, non-steroidal, anti-inflammatory drugs, ACE inhibitors, beta-blockers, analgesics, bronchodilators, spasmolytics, antihistamines, antibiotics, anti-tumor agents, and the like.

Although the invention has been illustrated by certain of the preceding examples, it is not to be construed as being limited thereby; but rather, the invention encompasses the generic area as disclosed herein. Various modifications and embodiments can be made without departing from the spirit and scope thereof.

What is claimed is:

1. A process for preparing optically active 2-arylcyclohexanols having the structural formula (II):

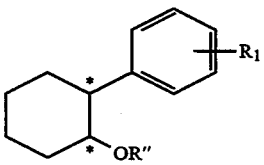

wherein $R_1$ is selected from the group consisting of hydrogen; a $C_{1-15}$ alkyl group; methoxymethyl group; methoxyethyl group; methylthiomethyl group; tetrahydropyranyl group; cyclopropylmethyl group; allyl group; cyclohexyl group; benzyl group; 9-anthrylmethyl group; t-butyldimethylsilyl group; phenyl group; naphthyl group; halogen; $NO_2$; $NR_2R_3$ where $R_2$ and $R_3$ are each independently H or $C_{1-15}$; $SO_3R_4$ where $R_4$ is H or $C_{1-15}$, —N($R_5$)—C(O)—$R_6$ where $R_5$ and $R_6$ are each independently H or $C_{1-15}$, —O—C(O)—$R_7$ where $R_7$ is H or $C_{1-15}$; and —$OR_8$ where $R_8$ is H or $C_{1-15}$; and R" is selected from the group H, $C_{1-15}$, —C(O)—R''' where R''' is from the group H, $C_{1-15}$, and halogenated $C_{1-15}$, and which process comprises the step of subjecting 1-arylcyclohexane-1,2-diols having the structural formula (I)

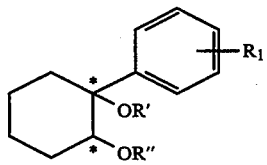

wherein $R_1$ and R" are the same as above in Formula II, and R' is the same as R", but R' and R" are each independently selected from their respective groups, to hydrogenolysis conditions for a sufficient period of time to form said 2-arylcyclohexanols of Formula II, said hydrogenolysis conditions comprising (a) a temperature of from about 0° to about 300° C. and (b) a pressure of from about one to about 200 atmospheres.

2. The process as set forth in claim 1 wherein said hydrogenolysis is carried out at a hydrogen pressure of from about one atmosphere to about 200 atmospheres.

3. The process as set forth in claim 2 wherein said hydrogenolysis is carried out in the presence of a hydrogenolysis catalyst.

4. The process as set forth in claim 3 wherein said hydrogenolysis catalyst is palladium.

5. The process as set forth in claim 3 wherein said hydrogenolysis catalyst is Raney nickel.

6. A process for preparing trans-(1R,2S)-2-phenylcyclohexanol and which comprises the step of subjecting (1R,2R)-2-phenylcyclohexane-1,2 diol to hydrogenolysis conditions for a sufficient period of time to form said cyclohexanol, said hydrogenolysis conditions comprising (a) a temperature of from about 0° C. to about 300° C. and (b) a pressure of about one atmosphere to about 200 atmospheres.

7. The process as set forth in claim 6 wherein said hydrogenolysis is carried out in the presence of a hydrogenolysis catalyst.

8. The process as set forth in claim 7 wherein said catalyst is Raney nickel.

9. The process as set forth in claim 8 wherein said catalyst is used in an amount whereby itself is the source also of hydrogen which dehydroxylates said diol to form said cyclohexanol.

10. The process as set forth in claim 9 wherein said hydrogenolysis is conducted in the presence of a solvent.

11. A process for preparing trans-(1S,2R)-2-phenylcyclohexanol and which comprises the step of subjecting (1S,2S)-2-phenylcyclohexane-1,2 diol to hydrogenolysis conditions to form said cyclohexanol, said hydrogenolysis conditions comprising (a) a temperature of from about 0° C. to about 300° C. and (b) a pressure of about one atmosphere to about 200 atmospheres.

12. The process as set forth in claim 11 wherein said hydrogenolysis is carried out in the presence of a hydrogenolysis catalyst.

13. The process as set forth in claim 12 wherein said catalyst is Raney nickel.

14. The process as set forth in claim 13 wherein said catalyst is used in an amount whereby itself is the source also of hydrogen which dehydroxylates said diol to form said cyclohexanol.

15. A process for preparing optically active cis-2-phenylcyclohexanols and which comprises the step of subjecting optically active cis-2-phenylcyclohexane-1,2 diols to hydrogenolysis conditions to form said cyclohexanols, said hydrogenolysis conditions comprising (a) a temperature of from about 0° C. to about 300° C. and (b) a pressure of about one atmosphere to about 200 atmospheres.

16. The process as set forth in claim 15 wherein said hydrogenolysis is carried out in the presence of a hydrogenolysis catalyst.

17. The process as set forth in claim 16 wherein said catalyst is palladium or palladium on carbon and the end product is (1R,2R)-2-phenylcyclohexanol.

18. The process as set forth in claim 16 wherein said catalyst is palladium or palladium on carbon and the end product is (1S,2S)-2-phenylcyclohexanol.

19. The process as set forth in claim 15 wherein said hydrogenolysis is carried out by the use of hydrogen which is present at from about one atmosphere to about 100 atmospheres.

20. The product produced by the process as set forth in claim 1.

* * * * *